US008636693B2

United States Patent
Schleicher (10) Patent No.: US 8,636,693 B2
(45) Date of Patent: Jan. 28, 2014

(54) PROPELLANT PILLOW

(75) Inventor: Brett Schleicher, New York, NY (US)

(73) Assignee: Palyon Medical Corporation, New York, NY (US)

( * ) Notice: Subject to any disclaimer, the term of this patent is extended or adjusted under 35 U.S.C. 154(b) by 0 days.

(21) Appl. No.: 13/095,258

(22) Filed: Apr. 27, 2011

(65) Prior Publication Data

US 2012/0277676 A1 Nov. 1, 2012

(51) Int. Cl.
*A61M 1/00* (2006.01)

(52) U.S. Cl.
USPC .......................................................... 604/151

(58) Field of Classification Search
USPC ......... 604/151, 140, 141, 143, 145, 131, 132, 604/93.01, 890.1, 891.1, 403, 408, 415
See application file for complete search history.

(56) References Cited

U.S. PATENT DOCUMENTS

| 4,518,684 | A | * | 5/1985 | Martin | 430/403 |
| 5,085,656 | A | | 2/1992 | Polaschegg | |
| 5,277,336 | A | * | 1/1994 | Youel | 222/105 |
| 5,336,194 | A | | 8/1994 | Polaschegg et al. | |
| 5,722,957 | A | | 3/1998 | Steinbach | |
| 5,814,019 | A | | 9/1998 | Steinbach et al. | |
| 5,836,915 | A | | 11/1998 | Steinbach et al. | |
| 6,730,060 | B1 | | 5/2004 | Steinbach et al. | |
| 6,994,699 | B2 | * | 2/2006 | Houwaert et al. | 604/408 |
| 7,637,892 | B2 | | 12/2009 | Steinbach et al. | |
| 7,708,730 | B2 | | 5/2010 | Steinbach et al. | |
| 7,914,510 | B2 | | 3/2011 | Steinbach et al. | |
| 2006/0259015 | A1 | | 11/2006 | Steinbach | |
| 2006/0259016 | A1 | | 11/2006 | Steinbach | |
| 2006/0271021 | A1 | | 11/2006 | Steinbach | |
| 2006/0271022 | A1 | | 11/2006 | Steinbach et al. | |
| 2007/0005044 | A1 | | 1/2007 | Steinbach et al. | |
| 2010/0069892 | A1 | | 3/2010 | Steinbach et al. | |
| 2011/0106010 | A1 | * | 5/2011 | Steinbach et al. | 604/140 |

* cited by examiner

*Primary Examiner* — Laura Bouchelle
*Assistant Examiner* — Niyati D Shah
(74) *Attorney, Agent, or Firm* — Lerner, David, Littenberg, Krumholz & Mentlik, LLP (57) ABSTRACT

A propellant pillow for use in an implantable pump is described herein. The propellant pillow generally includes a propellant bag having a septum attached thereto. In one embodiment, the pillow may further include a rigid member associated with the propellant bag to prevent piercing of the bag by an injection device inserted through the septum during a filling process. In another embodiment, the propellant pillow includes a propellant bag having a surrounding layer of resealable material encompassing the bag. The surrounding layer also serves to prevent piercing of the bag during filling of the pillow with a propellant. Methods of filling such propellant pillows with propellant as well as utilizing such pillows in connection with implantable pumps are also described herein.

18 Claims, 7 Drawing Sheets

PROPELLANT PILLOW

BACKGROUND OF THE INVENTION

The present invention relates to a propellant pillow for use in filling a propellant chamber of an implantable pump, in particular, a propellant pillow that contains structure designed to prevent damage to the pillow during filling of the pillow with a propellant.

Implantable pumps have been well known and widely utilized for many years. Typically, such pumps are implanted into patients who require the delivery of active substances or medicaments to specific areas of their body. For instance, patients who are experiencing severe pain may require pain killers daily or multiple times per day. Absent the use of an implantable pump or the like, a patient of this type would be subjected to one or more painful injections of medication multiple times during the course of the day. In the case of pain associated with more remote areas of the body, such as the spine, these injections may be extremely difficult to administer and particularly painful for the patient. Moreover, attempting to treat conditions like these through oral or intravascular administration of medication often requires higher doses of such medication. This may cause severe side effects. Thus, it is widely recognized that utilizing an implantable pump may be beneficial to both the patient and the treating physicians.

Many implantable pump designs have been proposed, including pumps employing mechanical means and gas pressure driven propellant means for expelling fluids or active substances from the pump. The present invention is directly related to the latter. More particularly, the apparatus and methods taught in the present application are capable of being utilized with many different types of gas driven pumps, such as those shown in U.S. Pat. Nos. 4,969,873; 5,085,656; 5,336,194; 5,836,915; 5,722,957; 5,814,019; 5,766,150; and 6,730,060, as well as U.S. Patent Application Publication Nos. 2006/0259015, 2006/0259016, 2006/0271021, 2006/021022, 2007/0005044, and 2007/0112328, and U.S. patent application Ser. No. 12/609,385. The disclosure of each of the above-noted patents and patent applications are hereby incorporated by reference herein, and certain of these references may be referred to throughout the present application.

Figure 1:
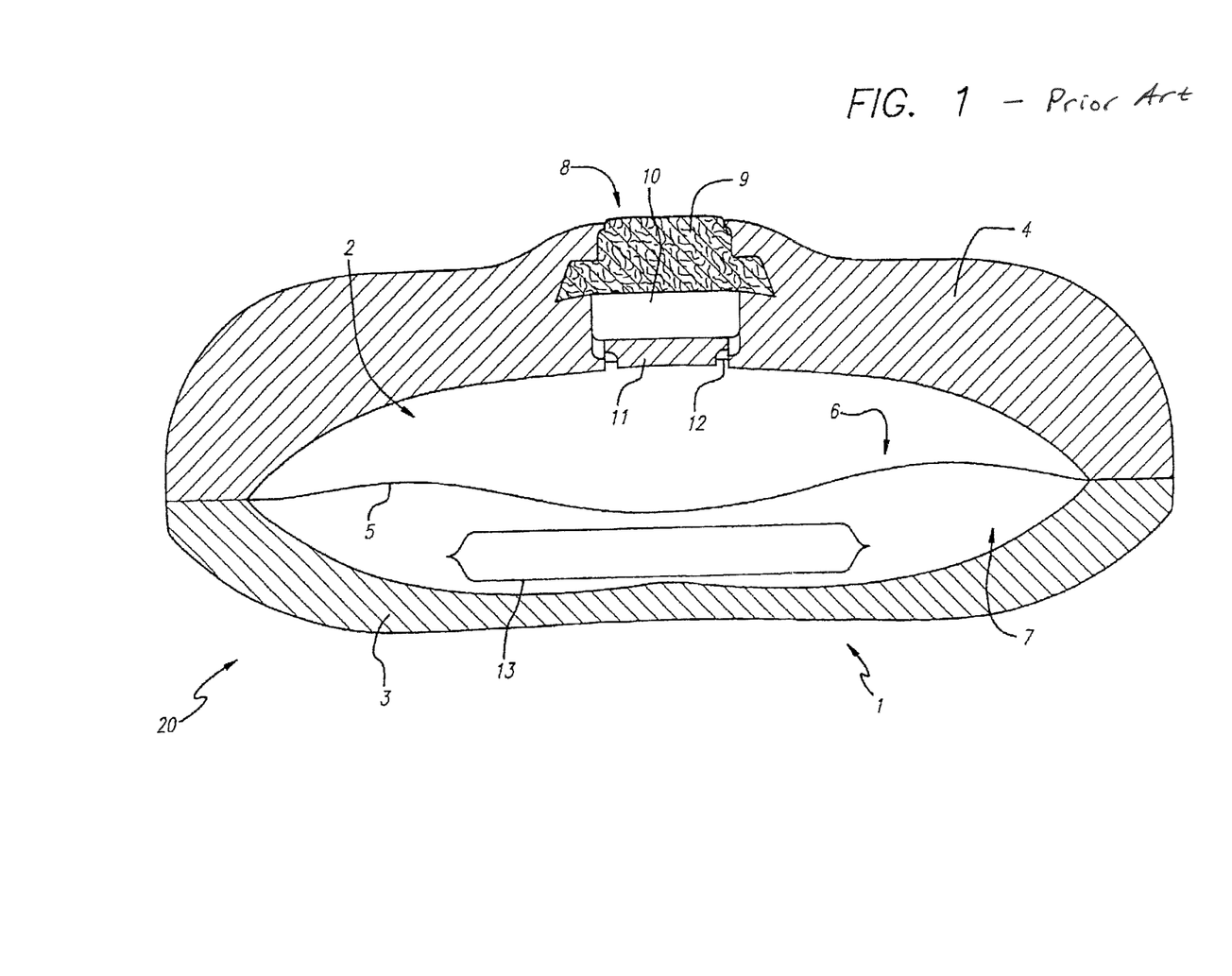
FIG. 1 is a cross-sectional side view of a prior art implantable pump having a propellant pillow disposed within a propellant chamber.
Figure 2:
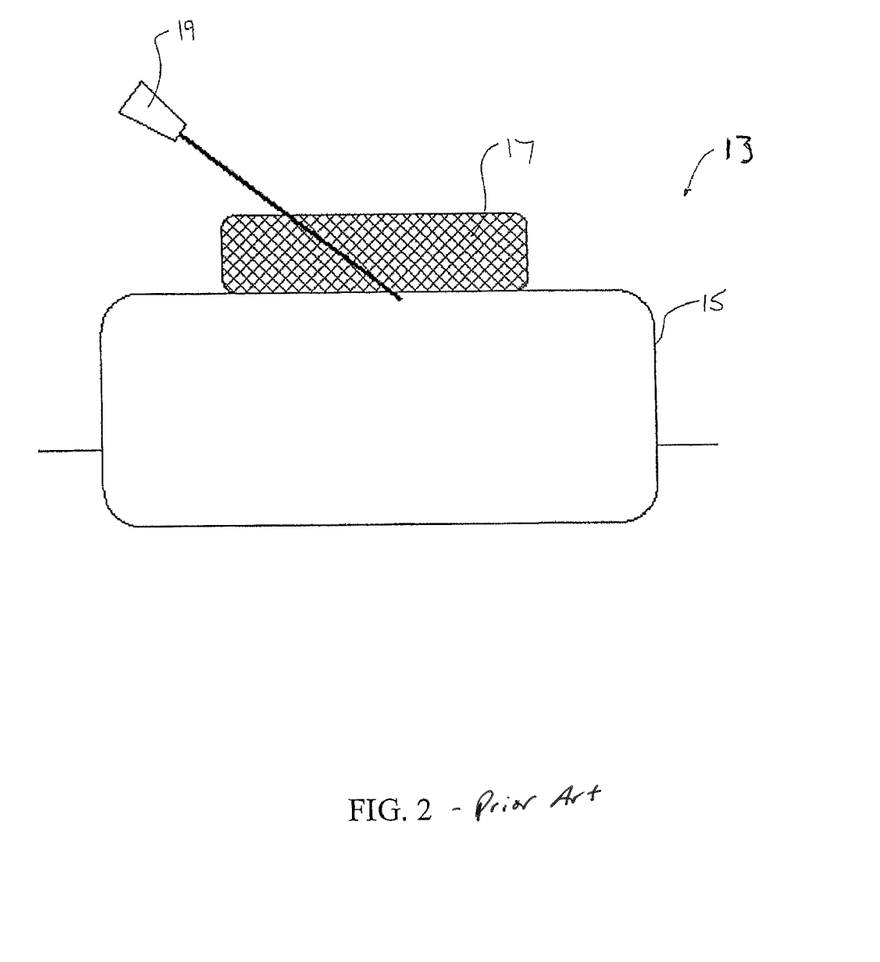
FIG. 2 is an enlarged cross-sectional illustration of the propellant pillow shown in FIG. 1 with an injection device inserted therein.

In general, gas driven implantable pumps, like those taught in each of the above-noted patents and patent applications, utilize an expandable propellant (e.g., an isobarically expanding gas) that acts upon a membrane to push medicament or other fluid from the pump. A common problem with such pumps revolves around the filling of the propellant chamber with propellant. Above-noted U.S. Pat. No. 5,766,150 ("the '150 patent") discloses an apparatus and method for use in such a filling process. As is shown in FIG. 1 of the '150 patent (reprinted as FIG. 1 of the present case), that patent teaches the use of a propellant pillow 13, which is filled with a gas propellant and placed into a propellant chamber 7 of an implantable pump, the chamber 7 being associated with a membrane 5 that separates chamber 7 from a fluid/medicament storage chamber 6, as detailed below. The chamber is thereafter sealed. FIG. 2 shows pillow 13 in greater detail, in particular, the fact that the pillow includes a propellant bag 15 and septum 17 affixed to the bag, which are not labeled as such in the '150 patent. Because bag 15 consists of a material through which the propellant may defuse (i.e., a permeable material), the gas slowly diffuses through the wall of the pillow and into chamber 7. Thus, the use of pillow 13 allows time for the propellant chamber and the remainder of the pump to be assembled before the gas escapes therefrom.

During assembly of a pump in accordance with the methods taught in the '150 Patent, the assembly steps first include punching bag 15 from an air padded foil or the like, evacuating it of all gases, and subsequently refilling it with a propellant. These steps generally involve the use of at least one syringe, cannula, needle, or the like (hereinafter referred to as an "injection device") 19 that pierces self-sealing silicone septum 17 to both evacuate all gases and introduce propellant. After being filled, pillow 13 is then introduced into a pump that has been divided into propellant chamber 7 and a fluid/medicament storage chamber 6. Subsequent to inserting pillow 13 into propellant chamber 7 of the pump, that chamber is sealed and evacuated of all gases. This allows the propellant to solely permeate through the walls of bag 15 and into propellant chamber 7. This method is generally applicable to any gas pressurized implantable pump, including the ones described in the various prior art references listed above and incorporated by reference herein.

While the device and methods taught in the '150 Patent have been utilized for some time in filling implantable pumps such as those disclosed above, they are not without their drawbacks. For instance, the initial evacuation of and subsequent filling of propellant within pillow 15 sometimes results in the structure of the bag being damaged by the injection device(s) 19. More particularly, evacuation of gas from bag 15 (i.e., creating a vacuum) causes the walls of the bag to collapse upon themselves and sometimes into contact with the point of the injection device(s). This may result in the walls being pierced, which thereby leads to a faster escape of the propellant from bag 15 than is desired. Thus, while the '150 Patent suggests placing the pillow within a sealed propellant chamber in approximately two minutes, this time period is significantly reduced when the bag walls are damaged. More often than not, this damage to pillow 13 results in less propellant ultimately being contained with the propellant chamber (as a vacuum may be applied to the propellant chamber before sealing it).

Figure 3:
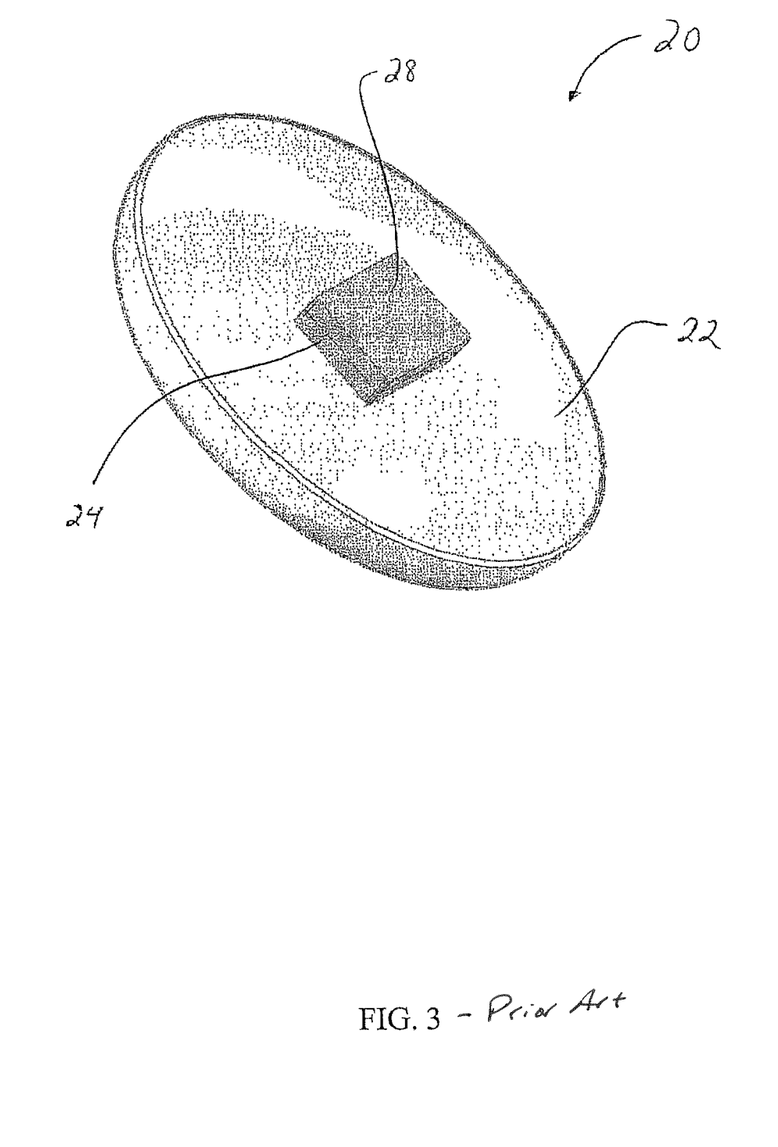
FIG. 3 is a perspective view of a propellant pillow in accordance with another existing propellant pillow design.
Figure 4:
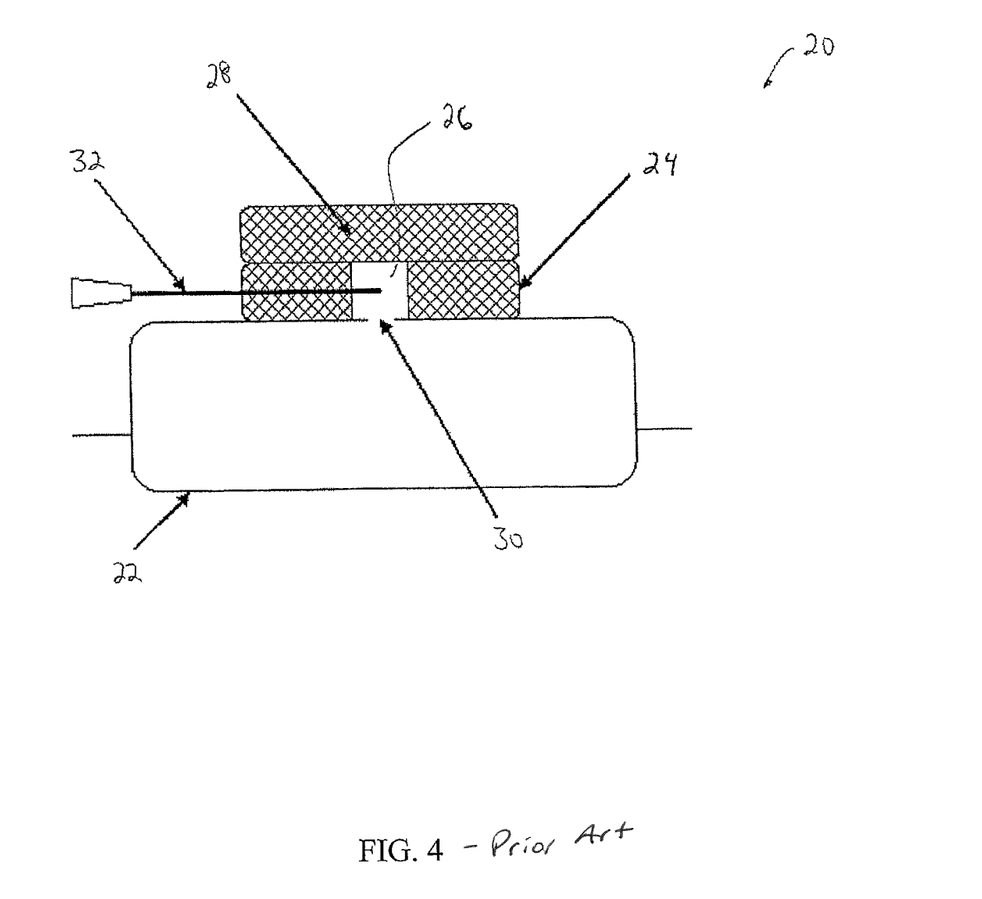
FIG. 4 is a cross-sectional side view of the propellant pillow shown in FIG. 3 with an injection device inserted therein.

Above-noted U.S. patent application Ser. No. 12/609,385 ("the '385 Application") discloses a propellant pillow that improves upon the one taught in the '150 Patent. As is shown in FIGS. 3 and 7 of the '385 Application (reprinted as FIGS. 3 and 4 of the present case), that application teaches the use of a propellant pillow 20 that includes a propellant bag 22, a first septum 24, including an opening 26, and a second septum 28 overlying the first septum. At least one opening 30 is also preferably included in propellant bag 22. This design allows for an injection device 32 to be inserted laterally through first septum 24 until the tip of the injection device extends into opening 26 (best shown in FIG. 4). In this position, the injection device can be utilized to evacuate all air or other gas that is contained within propellant bag 22, such that the air or gas exits through opening 30 of propellant bag 22, into opening 26 of first septum 24, and through the injection device. Like in the propellant pillow taught in the '150 Patent, this evacuation step generally results in propellant bag 22 collapsing upon itself. However, because of the design of propellant pillow 20, injection device 32 is not permitted to engage any portion of propellant bag 22 during its collapse. The propellant bag can be filled in a like manner through opening 26 and first septum 24, through opening 30 and propellant bag 22, and into the propellant bag.

Although the above-discussed propellant bags and propellant filling techniques are indeed useful in the filling operation of a propellant bag of an implantable pump, such designs can be improved upon. Therefore, there exists a need for an improved propellant pillow for use in filling a propellant chamber of an implantable pump.

BRIEF SUMMARY OF THE INVENTION

A first aspect of the present invention is a pillow for use in filling a gas pressure driven implantable pump. In a preferred embodiment, the pillow includes a propellant bag for containing a propellant and a septum attached to the bag. A rigid member is also associated with the propellant bag, the rigid member serving to prevent piercing of the propellant bag by an injection device inserted through the septum.

In other embodiments according to the aforementioned first aspect, the propellant bag is formed of a permeable material facilitating release of the propellant therefrom. In such a case, the permeable material may be selected from the group consisting of polypropylene and polyethylene. Still other embodiments may employ a rigid member that is attached to a bottom surface of the propellant bag. Such embodiments may also include a rigid member unitarily formed with the bottom surface of the bag. In even further embodiments, the rigid member may be suspended within the propellant bag, and may in fact be attached to lateral sides of the bag facilitating suspension therein. Other embodiments include a septum that is made of a self-sealing material.

A second aspect of the present invention is a process for filing a propellant chamber of a gas pressure driven implantable pump with a propellant. One preferred embodiment of this second aspect includes the steps of providing a pump having a medicament chamber and a propellant chamber, providing a propellant pillow including a propellant bag, a septum attached to the bag and a rigid member associated with the bag, wherein the rigid member prevents piercing of the bag by an injection device inserted through the septum, filling the pillow with the propellant, wherein the filling step include inserting the injection device into the septum, inserting the pillow filled with the propellant into the propellant chamber, and closing the propellant chamber.

Other embodiments of this second aspect may further include the step of evacuating the propellant pillow of substantially all gases contained therein. The evacuating step may also be performed through the use of the injection device inserted into the septum. Further during the evacuating step, the injection device may contact the rigid member and be prevented from piercing the propellant bag. Such a rigid member may be attached to a bottom surface of the propellant bag or may also be suspended within the bag.

A third aspect of the present invention is another pillow for use in filling a gas pressure driven implantable pump. In accordance with one preferred embodiment of this third aspect, the pillow includes a propellant bag for containing a propellant and a resealable layer of material attached to and substantially surrounding the bag, wherein the resealable layer of material prevents the propellant from escaping the bag when an injection device is inserted through the layer of material.

In other embodiments of this third aspect, the layer of material may entirely encompass the propellant bag. The layer of material may also be composed of material selected from the group consisting of silicone and silicone rubber. Other embodiments include a propellant bag that has at least one weakened area facilitating rupture of the bag and allowing release of the propellant therefrom. Still further, the resealable layer may also have at least one weakened area facilitating rupture of the layer of material and allowing release of the propellant therefrom.

A fourth aspect of the present invention is another process for filing a propellant chamber of a gas pressure driven implantable pump with a propellant. One preferred embodiment of this fourth aspect includes the steps of providing a pump having a medicament chamber and a propellant chamber, providing a propellant pillow including a propellant bag and a resealable layer of material attached to and substantially surrounding the bag, wherein the resealable layer of material prevents the propellant from escaping the bag when an injection device is inserted through the layer of material, filling the pillow with the propellant, wherein the filling step includes inserting the injection device through the resealable layer of material, inserting the pillow filled with the propellant into the propellant chamber, closing the propellant chamber, and applying a force to the propellant pillow to facilitate rupturing of the pillow.

In other embodiments of this fourth aspect, the propellant pillow may have at least one weakened area facilitating rupture of the pillow and allowing release of the propellant therefrom.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION

In describing the preferred embodiments of the subject illustrated and to be described with respect to the drawings, specific terminology will be used for the sake of clarity. However, the invention is not intended to be limited to any specific terms used herein, and it is to be understood that each specific term includes all technical equivalents, which operate in a similar manner to accomplish a similar purpose.

Figure 5:
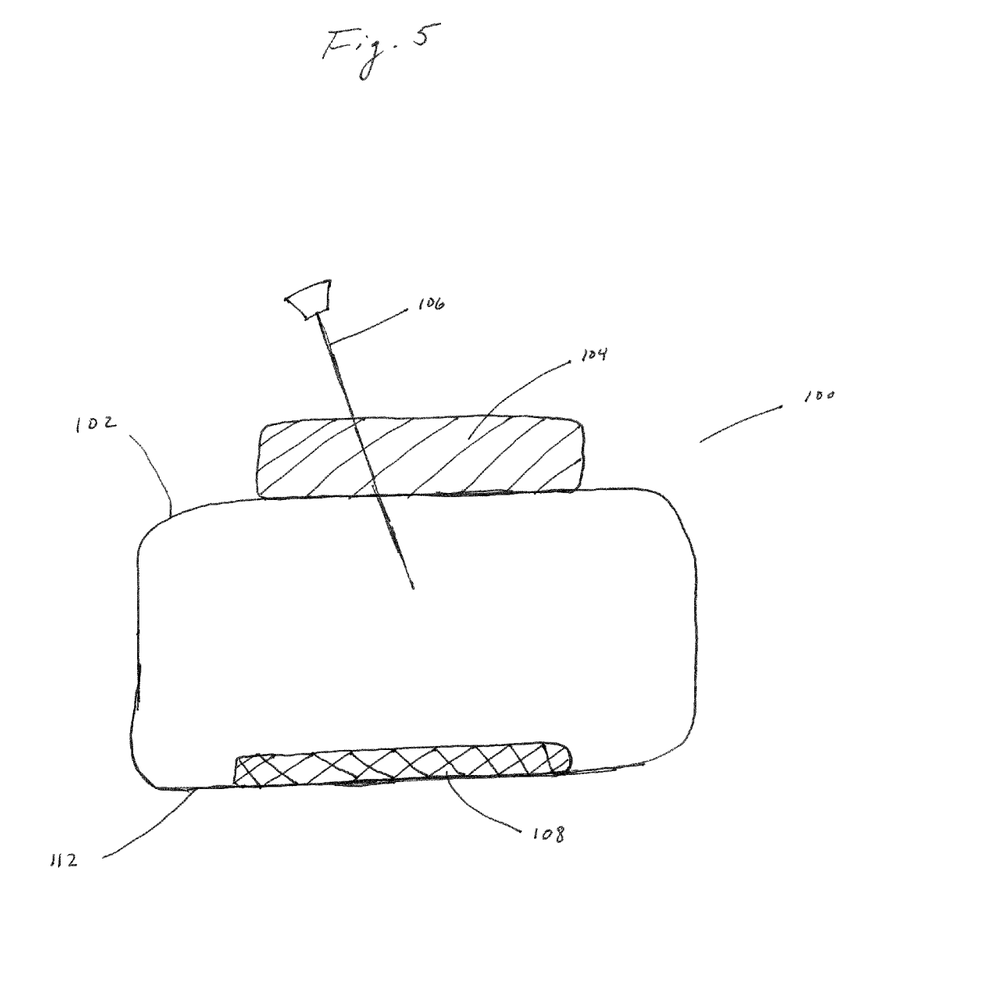
FIG. 5 is cross-sectional side view of a propellant pillow in accordance with one embodiment of the present invention.
Figure 6:
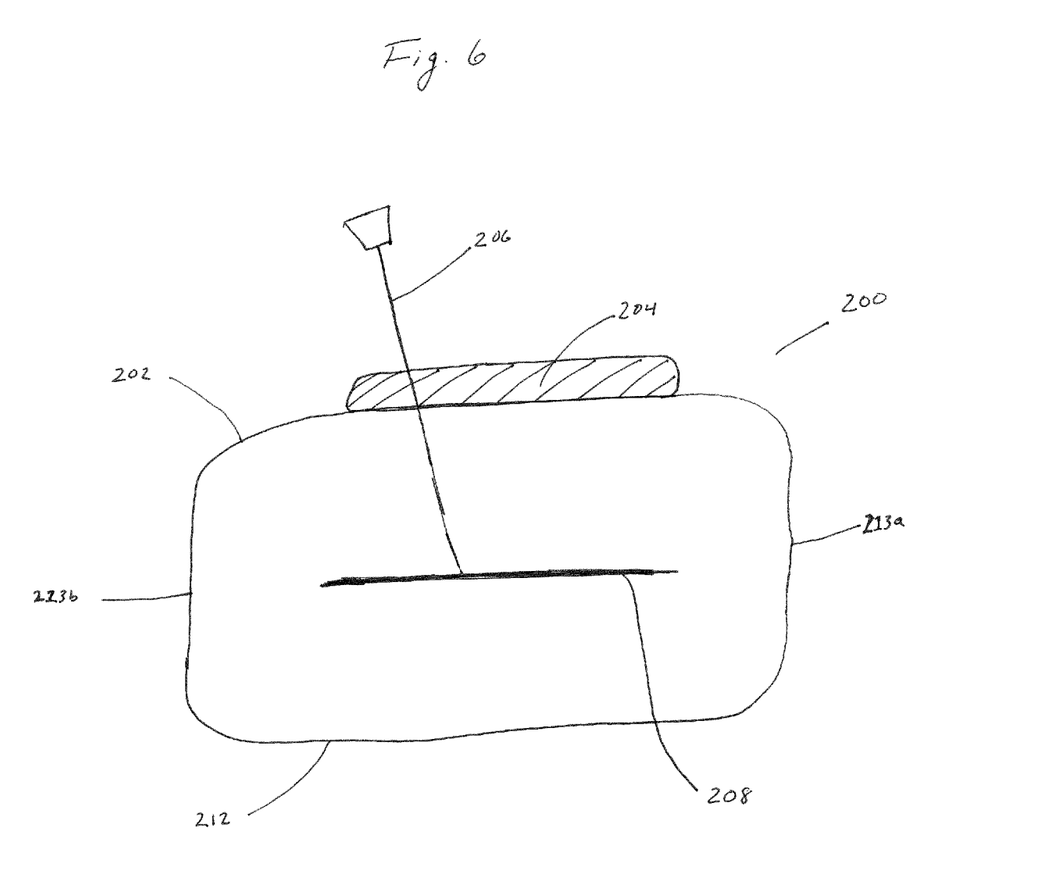
FIG. 6 is a cross-sectional side view of a propellant pillow in accordance with another embodiment of the present invention.
Figure 7:
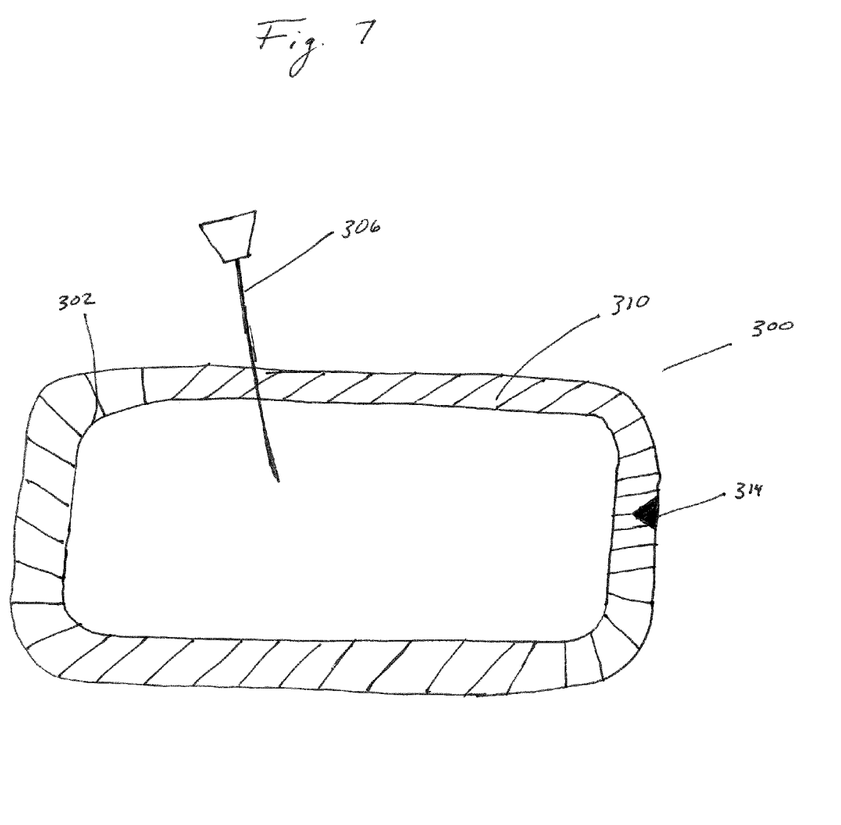
FIG. 7 is a cross-sectional side view of a propellant pillow in accordance with yet another embodiment of the present invention.

Referring to FIGS. 5-7, there are shown improved propellant pillows 100, 200 and 300, respectively, in accordance with the present invention. Each of the propellant pillows is designed for use in filling a propellant chamber of an implantable pump. As shown in FIGS. 5 and 6, pillows 100 and 200 each generally include a permeable propellant bag with a septum attached thereto, and a rigid member associated therewith. FIG. 7, on the other hand, depicts an alternate version pillow that includes a propellant bag substantially or entirely surrounded by a resealable layer of material. Each of these embodiment propellant pillows will now be discussed in detail.

Referring now to the embodiment shown in FIG. 5, propellant pillow 100 specifically includes a propellant bag 102 having a septum 104 attached thereto. Like in prior art pillows, propellant bag 102 is preferably constructed of polyolefins, such as polypropylene or polyethylene, and may be punched out from a larger sheet of similar bags. However, it is contemplated that any material suitable for containing a propellant utilized in an implantable pump and thereafter allowing such to permeate through its walls can be used. On the other hand, septum 104 is preferably created of silicone material, such as silicone rubber, but may be any material suitable for allowing resealing after the introduction of an injection device therethrough. As shown in FIG. 5, septum 104 is affixed to a top surface of the propellant bag 102, but may alternatively be affixed to any other surface on propellant bag 102. The preferred means of attaching septum 104 to bag 102 is through the use of glue or other adhesive, such as cyanacrylate. However, other means of attaching septum 104 to the propellant bag 102 may be utilized. For instance, septum 104 may be attached to bag 102 through a pressure sensitive adhesive such as a transfer adhesive or double sided tape.

As is further illustrated in FIG. 5, propellant pillow 100 also preferably contains a rigid member 108 within, which may be formed of any material having sufficient durability and hardness to prevent an injection device from piercing therethrough. Such materials may include, but are not limited to, plastics, metals, ceramics, composites, polycarbonate, polymethylmethacrylate (acrylic), ABS or ABS/PC blend, aluminum, titanium, 316L or 316LVM stainless steel, carbon fiber, and epoxy embedded fiberglass. Rigid member 108 is shown attached to the inside and along a bottom surface 112 of propellant bag 102. This ensures that injection device 106 placed through septum 104 will first contact member 108, rather than the material forming bag 102. Again, several different attachment means may be utilized, including the use of an adhesive, or through heat sealing. Rigid member 108 may also be formed integral or unitary with bag 102 in certain embodiments. This may require bag 102 to be specially manufactured.

Although shown generally centered and extending along a partial portion of bottom surface 112, rigid member 108 may be situated in any number of different arrangements. For instance, rigid member 108 may extend substantially across bottom surface 112 of bag 102 such that the member covers the entirety of bottom surface 112. Alternatively, rigid member 108 may be situated to cover several different portions of bottom surface 112, thus leaving several areas exposed. In this regard, rigid member 108 may cover the entirety of bottom surface 112 in a direction extending into and out of the page, but only a portion of bottom surface 112 in a left-to-right direction, as is shown in FIG. 5. Certain configurations could serve to reduce the cost of manufacturing pillow 100, while at the same time reducing the overall weight of the pillow, thus making the implantable pump assembly necessarily lighter. It is to be understood that the aforementioned configurations of rigid member 108 are solely illustrative and that the member may be arranged on bottom surface 112 of propellant bag 102 in any number of different ways so long as rigid member 108 is of sufficient size and shape to prevent an injection device from penetrating bottom surface 112 during filling of bag 102 with propellant.

FIG. 6 depicts an alternate embodiment pillow 200, which also includes a propellant bag 202, septum 204 and rigid member 208. However, instead of member 208 being situated along a bottom surface 212, the member is suspended within propellant bag 202. To achieve this suspension, rigid member 208 may be attached to lateral sides 213a and 213b of propellant bag 202 such that the member is raised above bottom surface 212. In this regard, upon forming of propellant bag 202, a film or netting (neither shown) may be heat sealed to the perimeter of bag 202 (including lateral sides 213a and 213b) and attached to rigid member 208 such that the film or netting may retain rigid member 208 above bottom surface 212. Alternatively, such film or netting may be attached to the perimeter of propellant bag 202 (including lateral sides 213a and 213b) through an adhesive process during the forming of bag 102. Rigid member 208 may be attached to the film or netting as described through a pressure sensitive adhesive such as a transfer adhesive or double sided tape. However, other similar means of attaching rigid member 208 to the film or netting are also contemplated.

In the above arrangements (i.e., with rigid member 208 being suspended above bottom surface 212 of bag 202), rigid member 208 may be generally defined by a circular center having flexible supports or the like projecting therefrom for attaching to the side of propellant bag 202, such that the supports engage the circular center of the rigid member 208 thus suspending member 208 above the bottom surface 212 of bag 202. These supports may in fact be heat sealed (or bonded by an adhesive) to the perimeter of bag 202 in a manner similar to that described above. Alternatively, rigid member 208 may be generally rectangular in shape and may extend laterally across bag 202 such that opposing ends of the member are attached directly to lateral sides 213a and 213b. In yet another configuration, rigid member 208 may form a cross shape such that the member is connected to bag 202 at the four ends of the cross. In each such configuration (e.g., rectangular or cross-shaped), rigid member 208 may in fact be heat sealed (or bonded by an adhesive) to bag 202 through a film or netting attached to both member 208 and bag 202, as described. It is to be understood that rigid member 208 may in fact be attached to propellant bag 202 at a number of different locations and may also be of any general shape provided that, like in above-discussed pillow 100, the rigid member sufficiently protects bag 202 from puncture by an injection device during a propellant filling process.

Propellant pillows 100 and 200 are preferably utilized in similar fashions to fill a propellant chamber of an implantable pump. Initially, an injection device 106, 206 is inserted through septum 104, 204 and into propellant bag 102, 202. In this position, the injection device is utilized to evacuate all air or other gasses contained within propellant bag 102, 202. Like in prior art propellant pillows (discussed above), this evacuation step generally results in propellant bag 102, 202 collapsing upon itself. However, due to the location and shape of rigid member 108, 208, the point of injection device 106, 206 cannot pierce any portion of propellant bag 102, 202. Specifically, during this evacuation step, rigid member 108, 208 acts as a shield, preventing the point of injection device 106, 206 from making contact with any portion of bag 102, 202. It is important to note that rigid member 108, 208 should be constructed in a manner in which bag 102, 202 is shielded regardless of the insertion angle or depth of injection device 106, 206.

Once the air or other gasses have been evacuated from propellant bag 102, 202, injection device 106, 206, or a subsequently inserted injection device, can be utilized to fill propellant bag 102, 202 with propellant. In the case of a subsequently inserted injection device, rigid member 108, 208 also preferably prevents inadvertent contact with bag 102, 202. After this filling step, the injection device may be removed from septum 104, 204, which preferably self-seals because of its material characteristics. In this state, propellant pillow 100, 200 is infused with gas that may only escape via a slow permeation through the diffusible material of propellant bag 102, 202. Thus, propellant pillow 100, 200 may be placed in the propellant chamber of an implantable pump, much like is discussed in the '150 Patent, and as is illustrated in FIGS. 8 and 9 of the '385 Application. In particular, propellant pillow 100, 200 may be placed between two flexible membranes of an implantable pump and thereafter left to permeate the propellant contained therein.

Once placed inside the propellant chamber of an implantable pump and after release of all propellant therefrom, it may be possible for propellant pillow 100, 200 to unexpectedly change its orientation within the propellant chamber. For instance, after insertion of propellant pillow 100, 200 into a propellant chamber, pillow 100, 200 may be able to change position such that rigid member 108, 208 is vertical rather than horizontal. In this orientation, a portion of rigid member 108, 208 could inadvertently contact the membrane of a medication chamber provided in the implantable pump leading to an unintended piercing of the same. It is therefore desirable to construct propellant pillow, 100, 200 so as to avoid any change in orientation as described. In this regard, rigid member 108, 208 may be composed of a magnetic material, with a corresponding piece of magnetic material also placed in a portion of the implantable pump (e.g., on a lower inside surface thereof) so as to exert a magnetic force on magnetic rigid member 108, 208. Magnetic rigid member 108, 208 may thusly be prevented from changing its orientation once inserted into the propellant chamber due to the magnetic force between rigid member 108, 208 and the corresponding magnetic material in the implantable pump.

Alternatively, pillow 100, 200 may be secured to a bottom surface of the propellant chamber during assembly through an adhesive or double sided tape, thusly preventing rigid member 108, 208 from changing its orientation after insertion. In yet another example, a film or netting similar to that described with respect to pillow 100, 200 may be placed inside the propellant chamber to secure pillow 100, 200 in a particular orientation and prevent rigid member 108, 208 from changing its orientation. Alternate methods of securing rigid member 108, 208 in a particular orientation may also be used.

Referring to FIG. 7, an alternate embodiment propellant pillow 300 is illustrated. Propellant pillow 300 preferably includes a propellant bag 302 that is substantially or entirely encompassed by a surrounding layer 310 of resealable material. Specifically, surrounding layer 310 may be composed of silicone material, such as silicone rubber, but may be any material suitable for allowing resealing after the introduction of an injection device therethrough. Thus, surrounding layer 310 is not unlike that of septum 104, 204. Alternatively, propellant pillow 300 may not contain a propellant bag and may in fact be formed entirely of surrounding layer 310. Surrounding layer 310, in this embodiment, may therefore serve to retain and selectively allow release of a propellant.

In the preferred embodiment, propellant bag 302 of pillow 300 is composed of a permeable material capable of housing any propellant therein. However, unlike above-discussed bags 102, 202, bag 302 is preferably capable of rupturing upon the application of a force, thereby releasing such propellant. Likewise, surrounding layer 310 is also preferably capable of rupturing upon the application of a force such that any propellant contained within bag 302 may fully escape therefrom. In the preferred embodiment shown in FIG. 7, surrounding layer 310 includes a weakened area 314 that facilitates such rupture. It is also contemplated that surrounding layer 310 may have multiple weakened areas 314 to facilitate rupture at multiple points. Similarly, propellant bag 302 may also have a weakened area corresponding to weakened area 314 and facilitating rupture of bag 302. Bag 302 may also have multiple weakened areas corresponding to multiple weakened areas 314 on surrounding layer 310. The weakened area(s) 314 as described may extend either partially or entirely through surrounding layer 310 (or bag 302) to facilitate rupture of the same. Alternatively, such weakened area(s) 314 may be in the form of a necked region in surrounding layer 310 (or bag 302) thus providing an area of reduced strength to facilitate rupture. It is also contemplated that weakened area(s) 314 may be formed of a different material than surrounding layer 310 (or bag 302), such material being more susceptible to breakage.

Propellant pillow 300 may be utilized in substantially the same manner as the propellant pillows discussed above, with some minor modifications. As with propellant pillows 100, 200, propellant pillow 300 is initially evacuated of all air or other gas through the use of an injection device 306, or the like. This step requires the injection device to pierce surrounding layer 310, and the resealable nature of the layer necessarily protects against inadvertent release of propellant from pillow 300, even when the pillow collapses upon itself. Again, like with pillows 100, 200, injection device 306, or a subsequently inserted injection device, is then utilized to fill propellant bag 302 with propellant. Puncture of the propellant bag 302 in this instance is not of great concern because of the design of surrounding layer 310. In this state, propellant pillow 300 is infused with gas that may only escape via a rupturing of bag 302 and surrounding layer 310.

Propellant pillow 300 is then placed in the propellant chamber of an implantable pump, in a similar fashion as is discussed above in connection with pillows 100, 200. At this stage, force may be applied to propellant pillow 300 such that propellant bag 302 and surrounding layer 310 are ruptured to release propellant into the propellant chamber. The force applied to pillow 300 may be in the form of pressure brought upon by increased heat. As an example, with pillow 300 inserted into a propellant chamber, an implantable pump as described may be inserted into the body of a patient. After such an insertion, the internal body temperature of the patient may cause any propellant within pillow 300 to heat, thereby causing the pressure in pillow 300 to increase. At the point that the pressure inside pillow 300 reaches a critical level, pillow 300 may rupture thus allowing release of the propellant therefrom. Alternatively, an operator such as a surgeon may grasp the propellant chamber in his/her hands (after insertion of pillow 300) and thereby apply body heat to pillow 300 and any propellant within. The surgeon or other operator may optionally squeeze or compress the propellant chamber, and thus pillow 300, with his/her hands as well. In this instance the heat generated by the surgeon's hands (and potentially the added force due to squeezing or compression) will cause pillow 300 to rupture, much like above. It is also contemplated that other external sources of heat may be used to heat pillow 300 (and any propellant within), such sources potentially including, for example, a heated liquid bath or a chamber of heated gasses.

As yet another option, the force applied to propellant pillow 300 may be applied solely by hand or an outside instrument. For instance, subsequent to the sealing of a propellant chamber (with pillow 300 disposed therein), an operator may apply a force by hand to the flexible membranes of the chamber, thereby rupturing pillow 300. In this regard, weakened area 314 should be designed to allow for rupture via a hand applied force, such as a flexing of the chamber and pillow. Alternatively, weakened area 314 could be designed so that an external tool, such as a hammer, mallet or pliers, is required to rupture pillow 300. However, it is important to note that weakened area 314 should be designed so that a force can be applied to rupture pillow 300 without damaging the propellant chamber. The inclusion of more than one weakened area 314 may allow for a faster or slower release of propellant from pillow 300 into the propellant chamber. Considering that the propellant chamber may be susceptible to damaging while utilizing an external tool as described, propellant pillow 300 may also be ruptured using such tools prior to insertion in the chamber of an implantable pump. In this regard, pillow 300 may be ruptured using any of the aforementioned external tools (or similar tools known in the art) and then quickly inserted into the propellant chamber to avoid undesired loss of propellant from pillow 300.

Other embodiment propellant pillows are also contemplated in accordance with the present invention. For instance, the aforementioned propellant bags may, instead of being punched from a sheet of previously formed bags, be formed through the use of two membranes of like permeable material joined to one another. In this regard, this may be an appropriate method of manufacturing a propellant bag with an integral or unitary rigid member, as is discussed above. Likewise, the rigid member depicted in pillows 100 and 200 may be formed of a resealable material, as is utilized in the septa of those devices. In such a case, puncture of the member will simply result in resealing upon withdrawal of the injection device. It is further to be understood that the various embodiments of propellant pillows discussed herein, as well as the methods of utilizing same, can be utilized in conjunction with many different implantable pumps. Certain examples are provided in the present application, but these are by no means meant to limit the use of the propellant pillow to such disclosed pumps. Finally, although circular propellant pillows are shown in the drawings, those pillows and their components may take on any shape suitable for use in placement in an implantable pump or the like.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An implantable pump system comprising:
a propellant pillow including:
 a propellant bag for containing a propellant;
 a self-sealing septum attached to the propellant bag; and
 a rigid member associated with the propellant bag, wherein the rigid member prevents piercing of the propellant bag by an injection device inserted through the septum; and
a fluid or medicament chamber associated with the propellant pillow, the fluid chamber being in communication with a conduit for delivering the fluid or medicament to a patient.

2. The system of claim 1, wherein the propellant bag is formed of a permeable material facilitating release of the propellant therefrom.

3. The system of claim 2, wherein the permeable material is selected from the group consisting of polypropylene and polyethylene.

4. The system of claim 1, wherein the rigid member is attached to a bottom surface of the propellant bag.

5. The system of claim 4, wherein the rigid member is unitarily formed with the bottom surface of the propellant bag.

6. The system of claim 1, wherein the rigid member is suspended within the propellant bag.

7. The system of claim 6, wherein the rigid member is attached to lateral sides of the propellant bag facilitating suspension therein.

8. A process for filling a propellant chamber of a gas pressure driven implantable pump with a propellant comprising the steps of:
providing an implantable pump system as claimed in claim 1, the implantable pump system further comprising a propellant chamber arranged adjacent to the fluid or medicament chamber;
filling the pillow with the propellant, wherein the filling step includes inserting the injection device into the septum;
inserting the pillow filled with the propellant into the propellant chamber; and
closing the propellant chamber.

9. The process of claim 8, further comprising the step of evacuating the pillow of substantially all gases contained therein.

10. The process of claim 9, wherein the evacuating step is performed through the use of the injection device inserted into the septum.

11. The process of claim 10, wherein, during the evacuating step, the injection device contacts the rigid member and is prevented from piercing the propellant bag.

12. The process of claim 11, wherein the rigid member is attached to a bottom surface of the propellant bag or is suspended within the bag.

13. An implantable pump system comprising:
a propellant pillow including a propellant bag for containing a propellant, a septum attached to the propellant bag, and a rigid member associated with the propellant bag, the rigid member preventing piercing of the propellant bag by an injection device inserted through the septum; and
a propellant chamber within which the propellant pillow is inserted, the propellant chamber being associated with a medicament or fluid, wherein the propellant chamber is adapted to expand upon release of propellant from the propellant bag to exert pressure on the medicament or fluid and deliver such medicament or fluid to a patient.

14. The implantable pump system of claim 13, wherein the propellant bag is formed of a permeable material facilitating release of the propellant therefrom.

15. The implantable pump system of claim 14, wherein the permeable material is selected from the group consisting of polypropylene and polyethylene.

16. The implantable pump system of claim 13, wherein the rigid member is attached to a bottom surface of the propellant bag.

17. The implantable pump system of claim 13, wherein the septum is self-sealing.

18. The implantable pump system of claim 13, wherein the medicament or fluid is contained in a medicament chamber separate from the propellant chamber, and a barrier separates the chambers, the barrier being acted upon by expansion of the propellant chamber upon release of release of propellant from the propellant bag.

* * * * *